United States Patent
Hogg et al.

(10) Patent No.: US 9,403,768 B2
(45) Date of Patent: Aug. 2, 2016

(54) INDOLINES

(71) Applicant: Hoffmann-La Roche Inc., Nutley, NJ (US)

(72) Inventors: Joan Heather Hogg, Los Altos Hills, CA (US); Stacy Remiszewski, Washington Township, NJ (US); Weiya Yun, Warren, NJ (US)

(73) Assignee: Hoffmann-La Roche Inc., Nutley, NJ (US)

(*) Notice: Subject to any disclaimer, the term of this patent is extended or adjusted under 35 U.S.C. 154(b) by 0 days.

(21) Appl. No.: 14/432,990

(22) PCT Filed: Oct. 1, 2013

(86) PCT No.: PCT/EP2013/070407
§ 371 (c)(1),
(2) Date: Apr. 1, 2015

(87) PCT Pub. No.: WO2014/056755
PCT Pub. Date: Apr. 17, 2014

(65) Prior Publication Data
US 2015/0246882 A1    Sep. 3, 2015

Related U.S. Application Data

(60) Provisional application No. 61/712,317, filed on Oct. 11, 2012.

(51) Int. Cl.
    *C07D 209/42*    (2006.01)
(52) U.S. Cl.
    CPC .................... *C07D 209/42* (2013.01)
(58) Field of Classification Search
    CPC .................................................. C07D 209/42
    See application file for complete search history.

(56) References Cited

FOREIGN PATENT DOCUMENTS

| WO | 2006017295 | 2/2006 |
|----|------------|--------|
| WO | 2010017035 | 2/2010 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
The International Search Report and Written Opinion, issued on Oct. 31, 2013, in the corresponding PCT Application No. PCT/EP2013/070407.

* cited by examiner

*Primary Examiner* — Shawquia Jackson

(57) ABSTRACT

Disclosed are compounds of Formula (I) or pharmaceutically acceptable salts thereof, wherein W, Y, Z, $R^1$, $R^2$, $R^3$ and $R^4$ are as described in this application, and methods of using said compounds in the treatment of cancer.

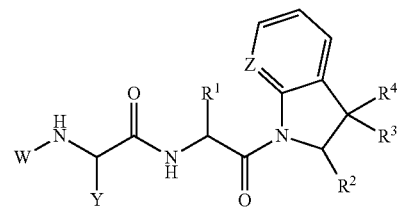

25 Claims, No Drawings

INDOLINES

CROSS-REFERENCE TO RELATED APPLICATIONS

This application is a National Stage Application of PCT/EP2013/070407 filed Oct. 1, 2013, which claims priority from U.S. Provisional Patent Application No. 61/712,317, filed on Oct. 11, 2012. The priority of both said PCT and U.S. Provisional Patent Application are claimed. Each of the prior mentioned applications is hereby incorporated by reference herein in its entirety.

FIELD OF THE INVENTION

The present invention relates to indolines which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors.

These compounds bind to the BIR2 and/or BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.1007/82_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPs: From caspase inhibitors to modulators of NF-κB, inflammation and cancer," Nature Review/Cancer, August 2010, Vol 10:561-574.

SUMMARY OF THE INVENTION

One aspect of the present invention is a compound of Formula I

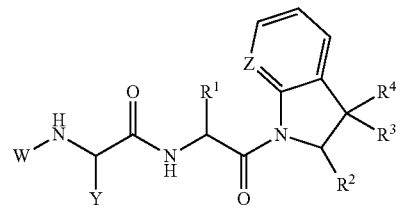

or pharmaceutically acceptable salts thereof, wherein W, Y, Z, $R^1$, $R^2$, $R^3$ and $R^4$ are as described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

"Alkyl" means a monovalent linear or branched saturated hydrocarbon of 1 to 12 carbon atoms. In particular embodiments, alkyl has 1 to 6 carbon atoms, and in more particular embodiments 1 to 4 carbon atoms. As used herein, "lower alkyl" denotes an alkyl group having from 1-6 carbon atoms ("$C_{1-6}$-alkyl"). Examples of alkyl include methyl, ethyl, propyl, isopropyl, butyl (also known as n-butyl), iso-butyl, sec-butyl, tert-butyl, pentyl, hexyl, and the like. The alkyl group can be optionally enriched in deuterium, e.g., —$CD_3$, —$CD_2CD_3$ and the like.

"Aryl" means a monovalent aromatic carbocyclic mono-, bi- or tricyclic ring system comprising 6 to 19 carbon ring atoms. Examples of aryl moieties include, but are not limited to, phenyl, naphthyl (also known as naphthalenyl), tolyl, xylyl, pyridinyl, quinolinyl, pyrimidinyl, imidazolyl, thiazolyl, anthracenyl, tetrazolyl, and fluorenyl.

"Benzoyl" means —C(=O)-phenyl.

"Benzyl" means —$CH_2$-phenyl.

"Halogen" or "Halo" means at atom selected from F, Cl, Br or I. In particular embodiments Halogen means F and Cl.

"$IC_{50}$" refers to the concentration of a particular compound required to inhibit 50% of a specific measured activity. $IC_{50}$ can be measured, inter alia, as is described subsequently in Example 13.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl or aryl means that the substitution (i.e. replacement of one hydrogen atom) can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

In one embodiment, the present invention relates to compounds of Formula I

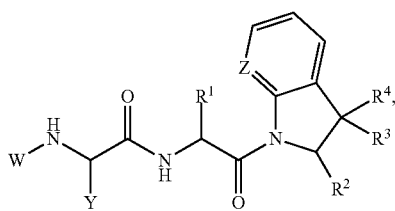

I wherein
W is selected from the group
a) lower alkyl that optionally includes 1-3 deuterium atoms,
b) lower alkyl that optionally may be substituted with $SO_2R^5$ and $OR^5$
Y is lower alkyl;
Z is CH;
$R^1$ is selected from the group
a) lower alkyl, and
b) aryl;
$R^2$ is $CONHR^6$;
$R^3$ and $R^4$ may be the same or different and each is independently selected from the group
a) H, and
b) lower alkyl;
$R^5$ is selected from the group
a) lower alkyl, and
b) aryl;
$R^6$ is selected from the group
a) H
b) aryl that optionally may be substituted with lower alkyl, $OR^5$, halogen, aryl, and $C(O)R^7$, and
c) lower alkyl that optionally may be substituted with aryl that optionally may be substituted with lower alkyl and halogen;
$R^7$ is selected from the group
a) lower alkyl, and
b) aryl;
or a pharmaceutically acceptable salt thereof.

In one embodiment, the present invention relates to compounds of Formula I, wherein
W is selected from the group
a) $C_{1-6}$-alkyl that optionally includes 1-3 deuterium atoms,
b) $C_{1-6}$-alkyl that optionally may be substituted with $SO_2R^5$ and $OR^5$
Y is $C_{1-6}$-alkyl;
Z is CH;
$R^1$ is selected from the group
a) $C_{1-6}$-alkyl, and
b) aryl;
$R^2$ is $CONHR^6$;
$R^3$ and $R^4$ may be the same or different and each is independently selected from the group
a) H, and
b) $C_{1-6}$-alkyl;
$R^5$ is selected from the group
a) $C_{1-6}$-alkyl, and
b) aryl;
$R^6$ is selected from the group
a) H
b) aryl that optionally may be substituted with $C_{1-6}$-alkyl, $OR^5$, halogen, aryl, and $C(O)R^7$, and
c) $C_{1-6}$-alkyl that optionally may be substituted with aryl that optionally may be substituted with $C_{1-6}$-alkyl and halogen;
$R^7$ is selected from the group
a) $C_{1-6}$-alkyl, and
b) aryl;
or a pharmaceutically acceptable salt thereof.

In one embodiment, the present invention relates to compounds of Formula I, wherein
W is $C_{1-6}$-alkyl,
Y is $C_{1-6}$-alkyl;
Z is CH;
$R^1$ is $C_{1-6}$-alkyl,
$R^3$ and $R^4$ may be the same or different and each is independently selected from the group
a) H, and
b) $C_{1-6}$-alkyl;
$R^6$ is selected from the group
a) H
b) aryl that optionally may be substituted with $C_{1-6}$-alkyl, $O-C_{1-6}$-alkyl, halogen, aryl, and C(O)-aryl, and
c) $C_{1-6}$-alkyl that optionally may be substituted with aryl that optionally may be substituted with $C_{1-6}$-alkyl and halogen;
or a pharmaceutically acceptable salt thereof.

In one embodiment, the present invention relates to compounds of Formula I, wherein
W is methyl,
Y is methyl;
Z is CH;
$R^1$ is isopropyl,
$R^3$ and $R^4$ are H,
$R^6$ is selected from the group
a) H
b) aryl that optionally may be substituted with $C_{1-6}$-alkyl, O—$C_{1-6}$-alkyl, halogen, aryl, and C(O)-aryl, and
c) $C_{1-6}$-alkyl that optionally may be substituted with aryl that optionally may be substituted with $C_{1-6}$-alkyl and halogen;
or a pharmaceutically acceptable salt thereof.

In one embodiment, the present invention relates to compounds of Formula I, wherein
W is methyl,
Y is methyl;
Z is CH;
$R^1$ is isopropyl,
$R^3$ and $R^4$ are H,
$R^6$ is selected from the group
a) H
b) phenyl that optionally may be substituted with F, methyl, methoxy, phenyl and C(O)-phenyl, and
c) $CH_2$-phenyl, wherein that phenyl optionally may be substituted with methyl and F;
or a pharmaceutically acceptable salt thereof.

In one embodiment, the present invention relates to compounds of Formula I, wherein W is methyl, Y is methyl, Z is CH, $R^1$ is isopropyl, $R^3$ and $R^4$ are H and $R^6$ is selected from the group H, difluorophenyl, benzyl, 5-fluoro-2-methyl-benzyl, benzoyl-phenyl, phenyl, diphenyl and methoxy-phenyl.
or a pharmaceutically acceptable salt thereof.

In one embodiment, the present invention relates to compounds of Formula I wherein W and Y are both $C_{1-6}$-alkyl, or a pharmaceutically acceptable salt thereof, or a pharmaceutically acceptable salt thereof.

In one embodiment, the present invention relates to compounds of Formula I wherein both W and Y are methyl, or a pharmaceutically acceptable salt thereof.

In one embodiment, the present invention relates to compounds of Formula I, wherein $R^1$ is $C_{1-6}$-alkyl, or a pharmaceutically acceptable salt thereof.

In one embodiment, the present invention relates to compounds of Formula I wherein $R^1$ is propanyl, or a pharmaceutically acceptable salt thereof.

In one embodiment, the present invention relates to compounds of Formula I, where $R^1$ is aryl, or a pharmaceutically acceptable salt thereof.

In one embodiment, the present invention relates to compounds of Formula I wherein $R^1$ is phenyl, or a pharmaceutically acceptable salt thereof.

In one embodiment, the present invention relates to compounds of Formula I, wherein $R^3$ and $R^4$ are H, or a pharmaceutically acceptable salt thereof.

In one embodiment, the present invention relates to compounds of Formula I, wherein one or both $R^3$ and $R^4$ are $C_{1-6}$-alkyl.

In one embodiment, the present invention relates to compounds of Formula I, where $R^5$ is $C_{1-6}$-alkyl, or a pharmaceutically acceptable salt thereof.

In one embodiment, the present invention relates to compounds of Formula I wherein $R^5$ is methyl, or a pharmaceutically acceptable salt thereof.

In one embodiment, the present invention relates to compounds of Formula I, wherein $R^5$ is aryl, or a pharmaceutically acceptable salt thereof, or a pharmaceutically acceptable salt thereof.

In one embodiment, the present invention relates to compounds of Formula I wherein $R^5$ is phenyl, or a pharmaceutically acceptable salt thereof.

In one embodiment, the present invention relates to compounds of Formula I, wherein $R^6$ is aryl that optionally may be substituted with $OR^5$, halogen, and aryl, or a pharmaceutically acceptable salt thereof.

In one embodiment, the present invention relates to compounds of Formula I, wherein $R^6$ is $C_{1-6}$-alkyl that optionally may be substituted with phenyl that optionally may be substituted with $C_{1-6}$-alkyl and halogen, or a pharmaceutically acceptable salt thereof.

In one embodiment, the present invention relates to compounds of Formula I wherein W, Y and $R^1$ are $C_{1-6}$-alkyl, $R^2$ is $CONHR^6$, and $R^6$ is aryl that optionally may be substituted with aryl, $C_{1-6}$-alkyl, and $OR^5$, or a pharmaceutically acceptable salt thereof.

In one embodiment, the present invention relates to compounds of Formula I wherein W, Y and $R^1$ are $C_{1-6}$-alkyl, $R^2$ is $CONHR^6$, and $R^6$ is H, or a pharmaceutically acceptable salt thereof.

In one embodiment, the present invention relates to compounds of Formula I wherein W, Y and $R^1$ are $C_{1-6}$-alkyl, $R^2$ is $CONHR^6$, and $R^6$ is $C_{1-6}$-alkyl that optionally may be substituted with phenyl that optionally may be substituted with halogen, or a pharmaceutically acceptable salt thereof.

In one embodiment, the present invention relates to compounds of Formula I wherein W, Y are $C_{1-6}$-alkyl, $R^1$ is aryl, $R^2$ is $CONHR^6$, and $R^6$ is aryl that optionally may be substituted with aryl, $C_{1-6}$-alkyl, halogen and $OR^5$, or a pharmaceutically acceptable salt thereof.

In one embodiment, the present invention relates to compounds of Formula I wherein $R^6$ is phenyl that optionally may be substituted with phenyl and $OR^5$, or a pharmaceutically acceptable salt thereof.

In one embodiment, the present invention relates to compounds of Formula I wherein W, Y are $C_{1-6}$-alkyl, $R^1$ is aryl, $R^2$ is $CONHR^6$, and $R^6$ is $C_{1-6}$-alkyl that optionally may be substituted with aryl that optionally may be substituted with halogen, or a pharmaceutically acceptable salt thereof.

In one embodiment, the present invention relates to compounds of Formula I wherein W, Y are $C_{1-6}$-alkyl, $R^1$ is aryl, $R^2$ is $CONHR^6$, and $R^6$ is H, or a pharmaceutically acceptable salt thereof.

In one embodiment, the present invention relates to compounds of Formula I selected from the group consisting of:
(S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide;
(S)-1-[(S)-3-Methyl-2-((S)-2-methylamino-propionylamino)-butyryl]-2,3-dihydro-1H-indole-2-carboxylic acid amide hydrochloride;
(S)-1-[(S)-3-Methyl-2-((S)-2-methylamino-propionylamino)-butyryl]-2,3-dihydro-1H-indole-2-carboxylic acid benzylamide;
(S)-1-[(S)-3-Methyl-2-((S)-2-methylamino-propionylamino)-butyryl]-2,3-dihydro-1H-indole-2-carboxylic acid 5-fluoro-2-methyl-benzylamide;
(S)-1-[(S)-3-Methyl-2-((S)-2-methylamino-propionylamino)-butyryl]-2,3-dihydro-1H-indole-2-carboxylic acid (2-benzoyl-phenyl)-amide;

(S)-1-[(S)-2-((S)-2-Methylamino-propionylamino)-2-phenyl-acetyl]-2,3-dihydro-1H-indole-2-carboxylic acid 5-fluoro-2-methyl-benzylamide hydrochloride;

(S)-1-[(S)-2-((S)-2-Methylamino-propionylamino)-2-phenyl-acetyl]-2,3-dihydro-1H-indole-2-carboxylic acid amide hydrochloride;

(S)-1-[(S)-2-((S)-2-Methylamino-propionylamino)-2-phenyl-acetyl]-2,3-dihydro-1H-indole-2-carboxylic acid phenylamide hydrochloride;

(S)-1-[(S)-2-((S)-2-Methylamino-propionylamino)-2-phenyl-acetyl]-2,3-dihydro-1H-indole-2-carboxylic acid biphenyl-2-ylamide hydrochloride;

(S)-1-[(S)-2-((S)-2-Methylamino-propionylamino)-2-phenyl-acetyl]-2,3-dihydro-1H-indole-2-carboxylic acid (2-methoxy-phenyl)-amide hydrochloride;

(S)-1-[(S)-2-((S)-2-Methylamino-propionylamino)-2-phenyl-acetyl]-2,3-dihydro-1H-indole-2-carboxylic acid 5-fluoro-2-methyl-benzylamide hydrochloride; and (S)-1-[(S)-3-Methyl-2-((S)-2-methylamino-propionylamino)-butyryl]-2,3-dihydro-1H-indole-2-carboxylic acid (2,6-difluoro-phenyl)-amide; or a pharmaceutically acceptable salt of any of the foregoing compounds.

In one embodiment, the present invention relates to compounds of Formula I selected from (S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide; and (S)-1-[(S)-3-Methyl-2-((S)-2-methylamino-propionylamino)-butyryl]-2,3-dihydro-1H-indole-2-carboxylic acid (2,6-difluoro-phenyl)-amide; or a pharmaceutically acceptable salt of either of the foregoing compounds.

In one embodiment, the present invention relates to a pharmaceutical composition comprising any of the compounds as described herein, or a pharmaceutically acceptable salt thereof, as an active ingredient together with a pharmaceutically acceptable carrier or excipient.

In one embodiment, the present invention relates to compounds of Formula I for use as a therapeutically active substance.

In one embodiment, the present invention relates to compounds of Formula I for use for the therapeutic and/or prophylactic treatment of cancer.

In one embodiment, the present invention relates to the use of a compound as described herein, or a pharmaceutically acceptable salt thereof, for the manufacture of a medicament for the therapeutic and/or prophylactic treatment of cancer.

In one embodiment, the present invention relates to a method of treating or ameliorating cancer comprising administering to a subject in need of such treatment a therapeutically effective amount of a compound as described herein.

One embodiment of the invention relates to compounds of Formula I where W and Y are both lower alkyl. In a particular embodiment W and Y are both methyl.

Another embodiment of the invention relates to compounds of Formula I where I where $R^1$ is lower alkyl, or a pharmaceutically acceptable salt thereof. In a particular embodiment $R^1$ is propanyl, or a pharmaceutically acceptable salt thereof.

Another embodiment of the invention relates to compounds of Formula I where $R^1$ is aryl, or a pharmaceutically acceptable salt thereof. In a particular embodiment $R^1$ is phenyl, or a pharmaceutically acceptable salt thereof.

Another embodiment of the invention relates to compounds of Formula I where $R^3$ and $R^4$ are H, or a pharmaceutically acceptable salt thereof.

Another embodiment of the invention relates to compounds of Formula I where one or both $R^3$ and $R^4$ are lower alkyl, or a pharmaceutically acceptable salt thereof.

Another embodiment of the invention relates to compounds of Formula I where $R^5$ is lower alkyl, or a pharmaceutically acceptable salt thereof. In a particular embodiment $R^5$ is methyl.

Another embodiment of the invention relates to compounds of Formula I where $R^5$ is aryl, or a pharmaceutically acceptable salt thereof. In a particular embodiment $R^5$ is phenyl.

Another embodiment of the invention relates to compounds of Formula I where $R^6$ is aryl that optionally may be substituted with $OR^5$, halogen, and aryl, or a pharmaceutically acceptable salt thereof.

Another embodiment of the invention relates to compounds of Formula I where $R^6$ is lower alkyl that optionally may be substituted with phenyl that optionally may be substituted with lower alkyl and halogen, or a pharmaceutically acceptable salt thereof.

Another embodiment of the invention relates to compounds of Formula I where W, Y and $R^1$ are lower alkyl, $R^2$ is $CONHR^6$ and $R^6$ is aryl that optionally may be substituted with aryl, lower alkyl, and $OR^5$, or a pharmaceutically acceptable salt thereof.

Another embodiment of the invention relates to compounds of Formula I where W, Y and $R^1$ are lower alkyl, $R^2$ is $CONHR^6$ and $R^6$ is H, or a pharmaceutically acceptable salt thereof.

Another embodiment of the invention relates to compounds of Formula I where W, Y and $R^1$ are lower alkyl, $R^2$ is $CONHR^6$ and $R^6$ is lower alkyl that optionally may be substituted with phenyl that optionally may be substituted with halogen, or a pharmaceutically acceptable salt thereof.

Another embodiment of the invention relates to compounds of Formula I where W, Y are lower alkyl, $R^1$ is aryl, $R^2$ is $CONHR^6$ and $R^6$ is aryl that optionally may be substituted with aryl, lower alkyl, halogen and $OR^5$, or a pharmaceutically acceptable salt thereof.

Another embodiment of the invention relates to compounds of Formula I where W, Y are lower alkyl, $R^1$ is aryl, $R^2$ is $CONHR^6$ and $R^6$ is lower alkyl that optionally may be substituted with aryl that optionally may be substituted with halogen, or a pharmaceutically acceptable salt thereof.

Another embodiment of the invention relates to compounds of Formula I where W, Y are lower alkyl, $R^1$ is aryl, $R^2$ is $CONHR^6$ and $R^6$ is H, or a pharmaceutically acceptable salt thereof.

Another embodiment of the invention relates to compounds of Formula I where W, Y are lower alkyl, $R^1$ is aryl, $R^2$ is $CONHR^6$ and $R^6$ is phenyl that optionally may be substituted with phenyl and $OR^5$, or a pharmaceutically acceptable salt thereof.

Compounds according to the invention wherein $R^6$ is H:
(S)-1-[(S)-3-Methyl-2-((S)-2-methylamino-propionylamino)-butyryl]-2,3-dihydro-1H-indole-2-carboxylic acid amide hydrochloride (Example 2); and
(S)-1-[(S)-2-((S)-2-Methylamino-propionylamino)-2-phenyl-acetyl]-2,3-dihydro-1H-indole-2-carboxylic acid amide hydrochloride (Example 7);
or a pharmaceutically acceptable salt of any of the foregoing compounds.

Compounds according to the invention wherein $R^6$ is aryl include:
(S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide (Example 1)

(S)-1-[(S)-3-Methyl-2-((S)-2-methylamino-propionylamino)-butyryl]-2,3-dihydro-1H-indole-2-carboxylic acid (2-benzoyl-phenyl)-amide (Example 5);

(S)-1-[(S)-2-((S)-2-Methylamino-propionylamino)-2-phenyl-acetyl]-2,3-dihydro-1H-indole-2-carboxylic acid phenylamide hydrochloride (Example 8);

(S)-1-[(S)-2-((S)-2-Methylamino-propionylamino)-2-phenyl-acetyl]-2,3-dihydro-1H-indole-2-carboxylic acid biphenyl-2-ylamide hydrochloride (Example 9);

(S)-1-[(S)-2-((S)-2-Methylamino-propionylamino)-2-phenyl-acetyl]-2,3-dihydro-1H-indole-2-carboxylic acid (2-methoxy-phenyl)-amide hydrochloride (Example 10); and (S)-1-[(S)-3-Methyl-2-((S)-2-methylamino-propionylamino)-butyryl]-2,3-dihydro-1H-indole-2-carboxylic acid (2,6-difluoro-phenyl)-amide (Example 12);

or a pharmaceutically acceptable salt of any of the foregoing compounds.

Compounds according to the invention wherein $R^6$ is lower alkyl include:

(S)-1-[(S)-3-Methyl-2-((S)-2-methylamino-propionylamino)-butyryl]-2,3-dihydro-1H-indole-2-carboxylic acid benzylamide (Example 3);

(S)-1-[(S)-3-Methyl-2-((S)-2-methylamino-propionylamino)-butyryl]-2,3-dihydro-1H-indole-2-carboxylic acid 5-fluoro-2-methyl-benzylamide (Example 4);

(S)-1-[(S)-2-((S)-2-Methylamino-propionylamino)-2-phenyl-acetyl]-2,3-dihydro-1H-indole-2-carboxylic acid 5-fluoro-2-methyl-benzylamide hydrochloride (Example 6); and (S)-1-[(S)-2-((S)-2-Methylamino-propionylamino)-2-phenyl-acetyl]-2,3-dihydro-1H-indole-2-carboxylic acid 5-fluoro-2-methyl-benzylamide hydrochloride (Example 11); or a pharmaceutically acceptable salt of any of the foregoing compounds.

A particular embodiment relates to the following compounds:

(S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide (Example 1); and (S)-1-[(S)-3-Methyl-2-((S)-2-methylamino-propionylamino)-butyryl]-2,3-dihydro-1H-indole-2-carboxylic acid (2,6-difluoro-phenyl)-amide (Example 12);

or a pharmaceutically acceptable salt of either of the foregoing compounds.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, $H_2O$, polyols, saccharose, invert sugar, glucose, etc. Suitable adjuvants for injection solutions are, for example, $H_2O$, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in the schemes below.

Scheme 1

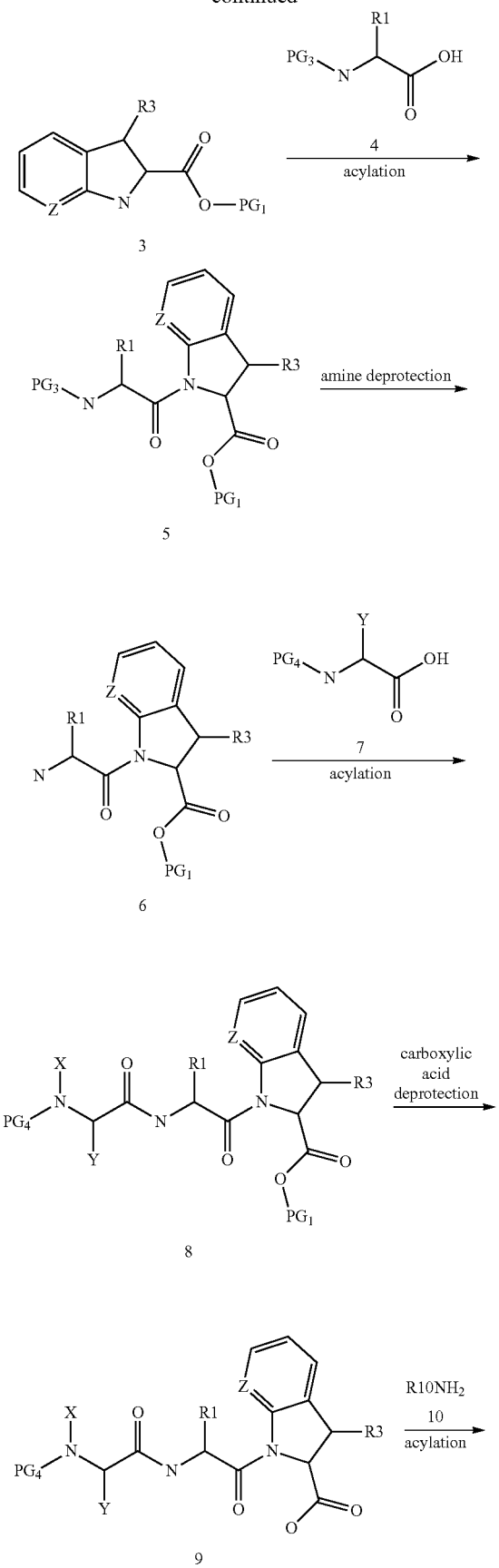

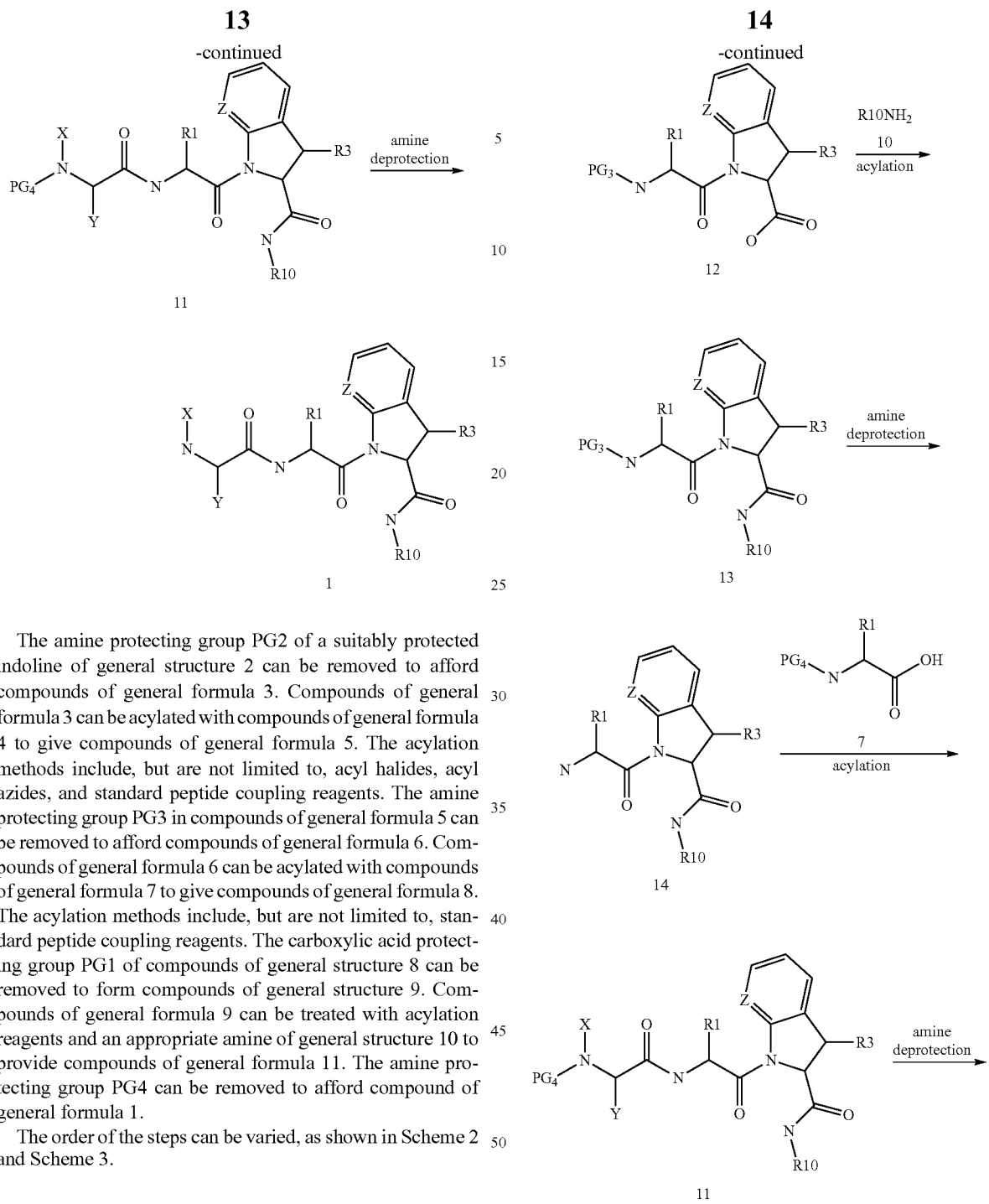

The amine protecting group PG2 of a suitably protected indoline of general structure 2 can be removed to afford compounds of general formula 3. Compounds of general formula 3 can be acylated with compounds of general formula 4 to give compounds of general formula 5. The acylation methods include, but are not limited to, acyl halides, acyl azides, and standard peptide coupling reagents. The amine protecting group PG3 in compounds of general formula 5 can be removed to afford compounds of general formula 6. Compounds of general formula 6 can be acylated with compounds of general formula 7 to give compounds of general formula 8. The acylation methods include, but are not limited to, standard peptide coupling reagents. The carboxylic acid protecting group PG1 of compounds of general structure 8 can be removed to form compounds of general structure 9. Compounds of general formula 9 can be treated with acylation reagents and an appropriate amine of general structure 10 to provide compounds of general formula 11. The amine protecting group PG4 can be removed to afford compound of general formula 1.

The order of the steps can be varied, as shown in Scheme 2 and Scheme 3.

Scheme 2

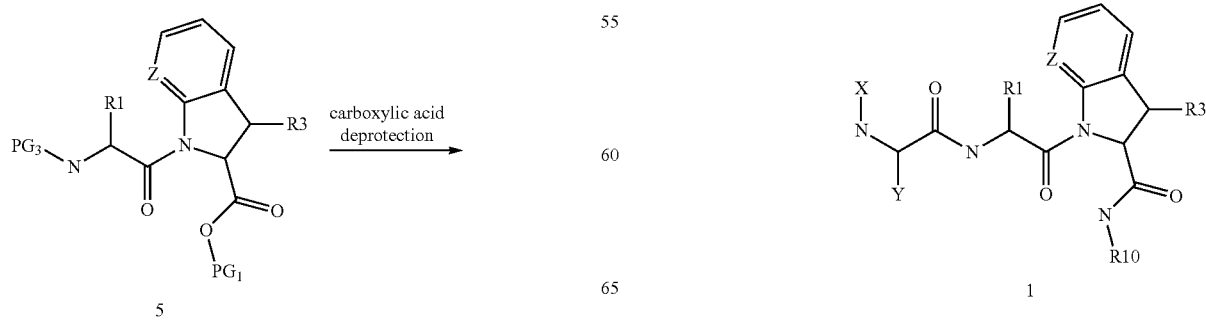

Scheme 3

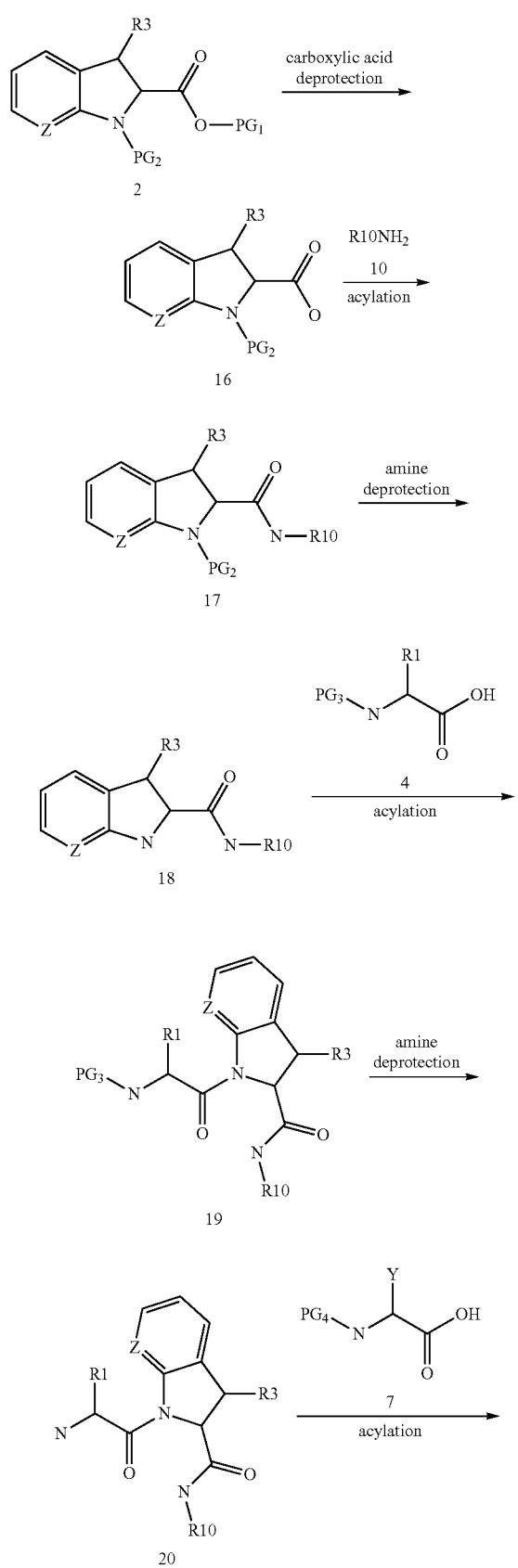

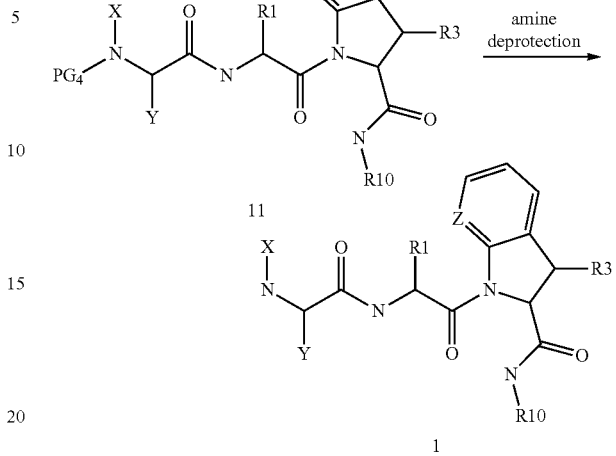

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2 (function in ISIS Draw, Elsevier/MDL), or AutoNom 2000 TT v4.01.305 (Elsevier/MDL), or functions available in ChemDraw Pro Control 11.0.2 (CambridgeSoft Corp.), or Struct=Name feature of electronic notebooks.

Example 1

(S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide

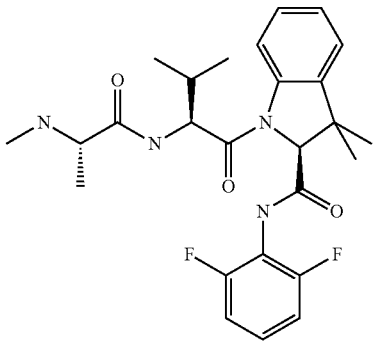

Step 1: To a solution of ethyl 3,3-dimethylindoline-2-carboxylate (prepared according to C. Rose et al. U.S. Pat. No. 6,403,561) (0.2 g, 912 μmol, Eq: 1.00) in DCM (2 mL) was added Boc-anhydride (0.32 g, 340 μL, 1.47 mmol, Eq: 1.61) and the resulting solution was stirred at rt for 72 h. The crude reaction mixture was applied directly to a silica column and purified by flash chromatography (silica gel, 24 g, 0% to 100% EtOAc in hexanes) to give 1-tert-butyl 2-ethyl 3,3-dimethylindoline-1,2-dicarboxylate as a colorless oil (240 mg), m/z=320 (M+H).

Step 2: To a solution of 1-tert-butyl 2-ethyl 3,3-dimethylindoline-1,2-dicarboxylate (0.25 g, 783 μmol, Eq: 1.00) in THF (3.2 mL)/MeOH (1.8 mL) was added lithium hydroxide (126 mg, 5.26 mmol, Eq: 6.72) dissolved in water (1 mL) and the resulting suspension was heated at 50° C. for 36 h. The reaction mixture was concentrated in vacuo and then the residue was taken up in water and washed with diethyl ether. The aqueous layer was then carefully acidified to pH~3 with 1 M aqueous HCl and extracted with EtOAc. The combined organic layers were concentrated in vacuo to give 1-(tert-butoxycarbonyl)-3,3-dimethylindoline-2-carboxylic acid as a white foam (220 mg), m/z=292 (M+H).

Step 3: Phosphorus oxychloride (74.0 mg, 0.045 mL, 483 μmol, Eq: 2.2) was added dropwise to a solution of 1-(tert-butoxycarbonyl)-3,3-dimethylindoline-2-carboxylic acid (64 mg, 220 μmol, Eq: 1.00) and 2,6-difluoroaniline (54.0 mg, 0.045 mL, 418 μmol, Eq: 1.9) in pyridine (1 mL) and the resulting dark yellow suspension stirred at rt overnight. The reaction mixture was diluted with water (10 mL) and extracted with EtOAc (2×10 mL). The combined organic layers were washed with water (10 mL), 0.1 M aqueous HCl (10 mL) and brine (5 mL) and concentrated in vacuo to give tert-butyl 2-(2,6-difluorophenylcarbamoyl)-3,3-dimethylindoline-1-carboxylate as a white solid (42 mg).

Step 4: TFA (1 mL, 13.0 mmol, Eq: 124) was added to a suspension of tert-butyl 2-(2,6-difluorophenylcarbamoyl)-3,3-dimethylindoline-1-carboxylate (42 mg, 104 μmol, Eq: 1.00) in DCM (1 mL) and the resulting yellow solution was stirred at rt for 1 h. The solution was then concentrated in vacuo and the residue treated with saturated aqueous NaHCO$_3$ (5 mL) and extracted with EtOAc. The combined organic layers were dried over Na$_2$SO$_4$ and concentrated in vacuo. The solid obtained (32 mg) was used without further purification.

Step 5: (S)-(9H-fluoren-9-yl)methyl 1-chloro-3-methyl-1-oxobutan-2-ylcarbamate (0.11 g, 307 μmol, Eq: 3.1) was added to a solution of N-(2,6-difluorophenyl)-3,3-dimethylindoline-2-carboxamide (30 mg, 99.2 μmol, Eq: 1.00) and pyridine (40 μL, 496 μmol, Eq: 5) in DCM (1 mL) and the resulting solution was stirred at rt for 3 h. The reaction mixture was diluted with EtOAc (20 mL) and washed with 1 M aqueous HCl (10 mL), 1 M aqueous NaOH (10 mL) and brine (10 mL), dried over Na$_2$SO$_4$ and concentrated in vacuo. The crude material was purified by flash chromatography (silica gel, 4 g, 0% to 30% EtOAc in hexanes) to give (S)-(9H-fluoren-9-yl)methyl 1-(2-(2,6-difluorophenylcarbamoyl)-3,3-dimethylindolin-1-yl)-3-methyl-1-oxobutan-2-ylcarbamate as a viscous oil (71 mg).

Step 6: Piperidine (0.1 mL, 1.01 mmol, Eq: 9.86) was added to a solution of (S)-(9H-fluoren-9-yl)methyl 1-(2-(2,6-difluorophenylcarbamoyl)-3,3-dimethylindolin-1-yl)-3-methyl-1-oxobutan-2-ylcarbamate (71 mg, 102 μmol, Eq: 1.00) in DCM (2 mL) and the resulting solution was stirred at rt for 3 h. The reaction mixture was concentrated in vacuo and the residue was purified by flash chromatography (silica gel, 4 g, 0% to 10% MeOH in DCM) to give (S)-1-(2-amino-3-methylbutanoyl)-N-(2,6-difluorophenyl)-3,3-dimethylindoline-2-carboxamide (32 mg).

Step 7: HATU (45 mg, 118 μmol, Eq: 1.48) was added to a solution of (S)-1-(2-amino-3-methylbutanoyl)-N-(2,6-difluorophenyl)-3,3-dimethylindoline-2-carboxamide (32 mg, 79.7 μmol, Eq: 1.00), (S)-2-(tert-butoxycarbonyl(methyl)amino)propanoic acid (20 mg, 98.4 μmol, Eq: 1.23) and diisopropylethylamine (50 μl, 286 μmol, Eq: 3.59) in DMF (1 mL) and the resulting yellow solution was stirred at rt for 1 h. The reaction mixture was diluted with EtOAc (10 mL) and washed with 0.1 M aqueous NaOH, 0.1 M aqueous HCl and brine and then concentrated in vacuo. The crude material was purified by flash chromatography (silica gel, 4 g, 0% to 50% EtOAc in hexanes) to give ((S)-1-{(S)-1-[(R)-2-(2,6-difluoro-phenylcarbamoyl)-3,3-dimethyl-2,3-dihydro-indole-1-carbonyl]-2-methyl-propylcarbamoyl})-ethyl)-methyl-carbamic acid tert-butyl ester (higher R$_f$, 15 mg) and ((S)-1-{(S)-1-[(S)-2-(2,6-difluoro-phenylcarbamoyl)-3,3-dimethyl-2,3-dihydro-indole-1-carbonyl]-2-methyl-propylcarbamoyl})-ethyl)-methyl-carbamic acid tert-butyl ester (lower R$_f$, 15 mg) along with some mixed fractions.

Step 8: TFA (0.5 mL, 6.49 mmol, Eq: 254) was added to a solution of and ((S)-1-{(S)-1-[(S)-2-(2,6-difluoro-phenylcarbamoyl)-3,3-dimethyl-2,3-dihydro-indole-1-carbonyl]-2-methyl-propylcarbamoyl})-ethyl)-methyl-carbamic acid tert-butyl ester (15 mg, 25.6 μmol, Eq: 1.00) in DCM (0.5 mL) and the resulting solution was stirred at rt for 3 h. The reaction was concentrated in vacuo, the residue was treated with saturated aqueous NaHCO$_3$ (2 mL) and the product was extracted into EtOAc. The organic layer was dried over Na$_2$SO$_4$ and concentrated in vacuo. Treatment of the residue with ether/hexanes gave (S)-3,3-dimethyl-1-[(S)-3-methyl-2-((S)-2-methylamino-propionylamino)-butyryl]-2,3-dihydro-1H-indole-2-carboxylic acid (2,6-difluoro-phenyl)-amide as a white powder (10 mg), m/z=487 (M+H).

Example 2

(S)-1-[(S)-2-((S)-2-Methylamino-propionylamino)-2-phenyl-acetyl]-2,3-dihydro-1H-indole-2-carboxylic acid amide

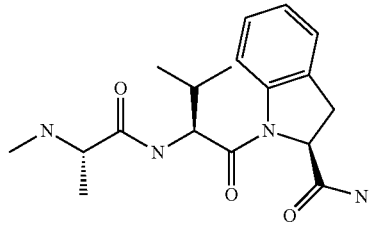 [SMILES: CN[C@@H](C)C(=O)N[C@H](C(=O)N1c2ccccc2C[C@H]1C(N)=O)C(C)C]

Step 1: To a solution of (S)-2-(tert-butoxycarbonyl(methyl)amino)propanoic acid (4.06 g, 20.0 mmol, Eq: 1), HOAT (4.08 g, 30.0 mmol, Eq: 1.5) and EDC (5.74 g, 30.0 mmol, Eq: 1.5) in DCM (200 mL), was added a solution of (S)-benzyl 2-amino-3-methylbutanoate hydrochloride (5.35 g, 22.0 mmol, Eq: 1.1) and N-methylmorpholine (4.45 g, 4.83 mL, 43.9 mmol, Eq: 2.2) in 50 mL of DCM. The reaction mixture was stirred at 23° C. for 3 h. The clear yellow solution was concentrated in vacuo. The residue was taken up in EtOAc and washed with saturated aqueous NaHCO$_3$ (1×300 mL), 5% aqueous KHSO$_4$ and brine (1×300 mL). The organic layer was dried over Na$_2$SO$_4$ and concentrated in vacuo. The crude material was purified by flash chromatography (silica gel, 0% to 80% EtOAc in hexanes) to afford (S)-2-[(S)-2-(tert-butoxycarbonyl-methyl-amino)-propionylamino]-3-methyl-butyric acid benzyl ester as a colorless oil (7.02 g), m/z=393 (M+H).

Step 2: (S)-2-[(S)-2-(tert-Butoxycarbonyl-methyl-amino)-propionylamino]-3-methyl-butyric acid benzyl ester (7 g, 18 mmol) and 1 M aqueous lithium hydroxide (40 mL, 40 mmol) was added to THF/MeOH/H$_2$O (3:1:1; 200 mL) to give a yellow solution. The reaction mixture was stirred at rt overnight and then concentrated in vacuo. The residue was dissolved in water and then acidified to pH 2 using first 6 M and then 1 M aqueous HCl. The mixture was extracted with EtOAc. The organic layer was dried over Na$_2$SO$_4$ and concentrated in vacuo to give crude (S)-2-[(S)-2-(tert-butoxycarbonyl-methyl-amino)-propionylamino]-3-methyl-butyric acid (5.7 g) which was used directly in the next step without further purification, m/z=303 (M+H).

Step 3: Cyanuric fluoride (3.25 g, 2.08 mL, 24.1 mmol) was added to a solution of (S)-2-[(S)-2-(tert-butoxycarbonyl-methyl-amino)-propionylamino]-3-methyl-butyric acid (5.4 g, 17.9 mmol) and pyridine (1.95 mL, 24.1 mmol) in CH$_2$Cl$_2$ (100 mL). The reaction mixture was stirred at 23° C. for 2.5 h. The resulting precipitate was filtered off and the mother liquor was concentrated. The residue was dissolved in EtOAc (250 mL), and the solution was washed with saturated NaHCO$_3$, 0.5 M citric acid and brine. The organic layer was dried over Na$_2$SO$_4$, filtered, concentrated and dried under vacuum. The resulting yellow oil was taken up in CH$_2$Cl$_2$ (35 mL) and cooled in a dry ice-MeOH bath. To this solution was added a solution of (S)-ethyl indoline-2-carboxylate (2.3 g, 12.0 mmol) and 2,6-di-tert-butylpyridine (4.6 g, 5.31 mL, 24.1 mmol) in 25 mL of CH$_2$Cl$_2$. The resulting mixture was stirred at rt overnight. The crude material was purified by flash chromatography (silica gel, 0% to 70% EtOAc in hexanes) to give (S)-1-{(S)-2-[(S)-2-(tert-butoxycarbonyl-methyl-amino)-propionylamino]-3-methyl-butyryl}-2,3-dihydro-1H-indole-2-carboxylic acid ethyl ester (2.93 g), m/z=476 (M+H).

Step 4: To a solution of (S)-1-{(S)-2-[(S)-2-(tert-butoxycarbonyl-methyl-amino)-propionylamino]-3-methyl-butyryl}-2,3-dihydro-1H-indole-2-carboxylic acid ethyl ester (2.93 g, 6.16 mmol) in THF/water/methanol (3:1:1; 60 mL) was added 1 M aqueous lithium hydroxide (18.5 mL, 18.5 mmol). The reaction mixture was stirred at 23° C. for 2.5 h and then concentrated in vacuo. The residue was diluted with water and acidified with 6 M and then 1 M aqueous HCl to pH~2. The mixture was extracted with EtOAc, the organic layer was dried over Na$_2$SO$_4$ and concentrated in vacuo to give (S)-1-{(S)-2-[(S)-2-(tert-butoxycarbonyl-methyl-amino)-propionylamino]-3-methyl-butyryl}-2,3-dihydro-1H-indole-2-carboxylic acid (2.70 g) as an off-white foam, m/z=470 (M+Na).

Step 5: (S)-1-{(S)-2-[(S)-2-(tert-butoxycarbonyl-methyl-amino)-propionylamino]-3-methyl-butyryl}-2,3-dihydro-1H-indole-2-carboxylic acid (60 mg, 134 μmol, Eq: 1) and EDC (77.1 mg, 402 μmol, Eq: 3) and HOAT (54.7 mg, 402 μmol, Eq: 3) were stirred in DMF (6 mL) for 10 min to give a light yellow solution. To this solution was added ammonium chloride (71.7 mg, 1.34 mmol, Eq: 10) and diisopropylethylamine (0.47 μL, 2.68 mmol, Eq: 20) in 2 mL of DMF. The mixture was stirred at rt overnight, and then concentrated in vacuo. The reaction mixture was poured into saturated aqueous NaHCO$_3$ (30 mL) and extracted with DCM (2×20 mL). The organic layer was washed with 0.5 M aqueous citric acid and brine, and then concentrated in vacuo. The crude material was purified by flash chromatography (silica gel, 0% to 90% EtOAc in hexanes) to afford {(S)-1-[(S)-1-((S)-2-carbamoyl-2,3-dihydro-indole-1-carbonyl)-2-methyl-propylcarbamoyl]-ethyl})-methyl-carbamic acid tert-butyl ester as an off-white powder (39 mg), m/z=447 (M+H).

Step 6: {(S)-1-[(S)-1-((S)-2-carbamoyl-2,3-dihydro-indole-1-carbonyl)-2-methyl-propylcarbamoyl]-ethyl})-methyl-carbamic acid tert-butyl ester (39 mg) was suspended in a 1:1 mixture of 4 M HCl in dioxane and DCM and stirred at rt for 1 h. The solvent was removed under reduced pressure and the solid was dissolved in CH$_3$CN and water (3:1), and lyophilized to give (S)-1-[(S)-2-((S)-2-methylamino-propionylamino)-2-phenyl-acetyl]-2,3-dihydro-1H-indole-2-carboxylic acid amide hydrochloride salt as a white powder (33 mg), m/z=347 (M+H).

The following examples in Table 1 were prepared using similar procedures as in Example 2 with the noted reactant modifications:

TABLE 1

| EX # | | Step 5 | m/z (M + H) |
|---|---|---|---|
| 3 | 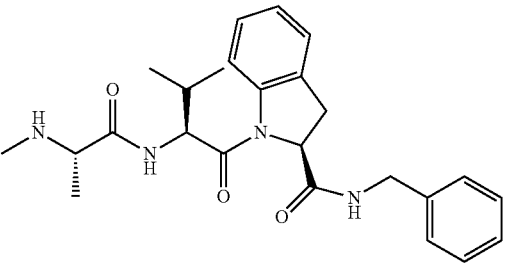 [SMILES: CN[C@@H](C)C(=O)N[C@H](C(=O)N1c2ccccc2C[C@H]1C(=O)NCc1ccccc1)C(C)C] | benzylamine | 437 |

TABLE 1-continued

| EX # | | Step 5 | m/z (M + H) |
|---|---|---|---|
| 4 | | 5-fluoro-2-methyl-benzylamine | 469 |
| 5 | | (2-aminophenyl)-phenyl-methanone | 527 |

Example 6

(S)-1-[(S)-2-((S)-2-Methylamino-propionylamino)-2-phenyl-acetyl]-2,3-dihydro-1H-indole-2-carboxylic acid 5-fluoro-2-methyl-benzylamide

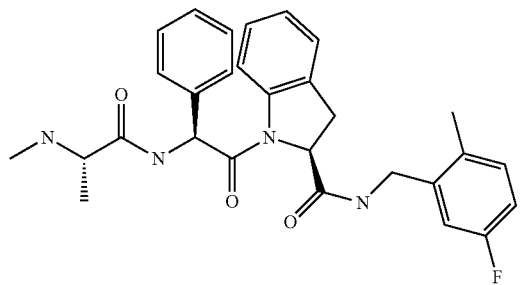 [SMILES: CN[C@@H](C)C(=O)N[C@H](C(=O)N1c2ccccc2C[C@H]1C(=O)NCc1cc(F)ccc1C)c1ccccc1]

Step 1: To a solution of (S)-2-(tert-butoxycarbonylamino)-2-phenylacetic acid (5.26 g, 20.9 mmol, Eq: 2) and pyridine (2.8 mL, 34.5 mmol, Eq: 3.3) in DCM (60 mL), cyanuric fluoride (4.66 g, 2.99 mL, 34.5 mmol, Eq: 3.3) was added. The reaction mixture was stirred at 23° C. for 2 h. The resulting precipitate was filtered off and the mother liquor was concentrated in vacuo. The residue was taken up in EtOAc, and washed with saturated aqueous NaHCO₃, 0.5 M aqueous citric acid and brine, and concentrated in vacuo. The light brown oil was taken up in DCM (20 mL) and cooled in an ice bath. To this acid fluoride solution was added a solution of (S)-ethyl indoline-2-carboxylate (2 g, 10.5 mmol, Eq: 1) and 2,6-di-tert-butylpyridine (4.00 g, 4.62 mL, 20.9 mmol, Eq: 2) in DCM (20 mL). The resulting mixture was stirred at rt overnight. The reaction was concentrated in vacuo and the crude material was purified by flash chromatography (silica gel, 5% to 20% EtOAc in hexanes) to give (S)-1-((S)-2-tert-butoxycarbonylamino-2-phenyl-acetyl)-2,3-dihydro-1H-indole-2-carboxylic acid ethyl ester (2.78 g) as a light yellow foam, m/z=425 (M+H).

Step 2: To (S)-1-((S)-2-tert-butoxycarbonylamino-2-phenyl-acetyl)-2,3-dihydro-1H-indole-2-carboxylic acid ethyl ester (2.78 g, 6.55 mmol, Eq: 1) was added 4 M HCl in dioxane (16.4 mL, 65.5 mmol, Eq: 10). The mixture was stirred at rt for 2 h. The solvent was removed in vacuo. After drying under vacuum, (S)-1-((S)-2-amino-2-phenyl-acetyl)-2,3-dihydro-1H-indole-2-carboxylic acid ethyl ester hydrochloride was obtained as an off-white solid which was used for next step without further purification.

Step 3: In a 50 mL round-bottomed flask, (S)-2-(tert-butoxycarbonyl(methyl)amino)propanoic acid (1.52 g, 7.48 mmol, Eq: 1.5) and HATU (1.9 g, 5 mmol, Eq: 1) were combined with DCM (20 mL) to give a light yellow suspension. (S)-1-((S)-2-amino-2-phenyl-acetyl)-2,3-dihydro-1H-indole-2-carboxylic acid ethyl ester hydrochloride (1.8 g, 5 mmol, Eq: 1) was added and followed by diisopropylethylamine (7 mL, 40 mmol, Eq: 8). The reaction was stirred at rt overnight. The crude reaction mixture was concentrated in vacuo, and then dissolved in EtOAc (75 mL). The solution was washed with water and brine, dried and concentrated in vacuo. The crude material was purified by flash chromatography (10% to 30% EtOAc in hexanes) to afford (S)-1-{(S)-2-[(S)-2-(tert-butoxycarbonyl-methyl-amino)-propionylamino]-2-phenyl-acetyl}-2,3-dihydro-1H-indole-2-carboxylic acid ethyl ester (2.3 g) as a white foam, m/z=510 (M+H).

Step 4: To a solution of (S)-1-{(S)-2-[(S)-2-(tert-butoxycarbonyl-methyl-amino)-propionylamino]-2-phenyl-acetyl}-2,3-dihydro-1H-indole-2-carboxylic acid ethyl ester (2.28 g, 4.47 mmol, Eq: 1) in 60 mL of THF/water/MeOH (3:1:1) was added 1 M aqueous lithium hydroxide (13.4 mL, 13.4 mmol, Eq: 3). The reaction mixture was stirred at 23° C. for 2.5 h. The reaction was concentrated in vacuo and the residue was taken up in water and acidified with 6 M and then 1 M aqueous HCl to pH~2. The mixture was extracted with EtOAc (2×50 mL) and the organic layers were combined, dried over Na$_2$SO$_4$ and concentrated in vacuo to afford (S)-1-{(S)-2-[(S)-2-(tert-butoxycarbonyl-methyl-amino)-propionylamino]-2-phenyl-acetyl}-2,3-dihydro-1H-indole-2-carboxylic acid as a white foam (2.04 g), m/z=482 (M+H).

Step 5: To a solution of (S)-1-{(S)-2-[(S)-2-(tert-butoxycarbonyl-methyl-amino)-propionylamino]-2-phenyl-acetyl}-2,3-dihydro-1H-indole-2-carboxylic acid (50 mg, 104 μmol, Eq: 1) and (5-fluoro-2-methylphenyl)methanamine (28.9 mg, 208 μmol, Eq: 2) in DCM (3 mL) cooled to 0° C. was added 2,4,6-tripropyl-1,3,5,2,4,6-trioxatriphosphorinane-2,4,6-trioxide (50% weight solution in EtOAc, volume added: 150 μL, Eq: 2) and diisopropylethylamine (54 μL, Eq: 3). The reaction mixture was stirred at 0° C. for 20 min and then at 23° C. for 1 h. The reaction was quenched with saturated aqueous NaHCO$_3$ to pH=8. The two phases were separated and aqueous phase was re-extracted with DCM. The organic layers were combined and concentrated in vacuo. The mixture was purified by flash chromatography (silica gel, 0% to 70% EtOAc in hexanes) to give ((S)-1-{(S)-2-[(S)-2-(5-fluoro-2-methyl-benzylcarbamoyl)-2,3-dihydro-indol-1-yl]-2-oxo-1-phenyl-ethylcarbamoyl})-ethyl)-methyl-carbamic acid tert-butyl ester as a white powder (49 mg), m/z=603 (M+H).

Step 6: ((S)-1-{(S)-2-[(S)-2-(5-Fluoro-2-methyl-benzylcarbamoyl)-2,3-dihydro-indol-1-yl]-2-oxo-1-phenyl-ethylcarbamoyl}-ethyl)-methyl-carbamic acid tert-butyl ester (48 mg) was suspended in a 1:1 mixture of 4 M HCl in dioxane) and DCM and stirred at rt for 1 h. The solvent was removed in vacuo and the resulting solid was dissolved in CH$_3$CN and water (3:1), and lyophilized to give (S)-1-[(S)-2-((S)-2-methylamino-propionylamino)-2-phenyl-acetyl]-2,3-dihydro-1H-indole-2-carboxylic acid 5-fluoro-2-methyl-benzylamide hydrochloride salt as a white powder (44 mg), m/z=503 (M+H).

The following examples in Table 2 were prepared using similar procedures as for Example 6 with the noted reactant modifications.

TABLE 2

| EX # | | | Step 5 | m/z (M + H) |
|---|---|---|---|---|
| 7 | ClH | | ammonium chloride | 381 |
| 8 | | | aniline | 457 |
| | ClH | | | |
| 9 | ClH | | biphenyl-2-ylamine | 533 |

TABLE 2-continued

| EX # | | Step 5 | m/z (M + H) |
|---|---|---|---|
| 10 | ClH | 2-methoxyaniline | 487 |
| 11 | | benzylamine | 471 |

Example 12

(S)-1-[(S)-3-Methyl-2-((S)-2-methylamino-propionylamino)-butyryl]-2,3-dihydro-1H-indole-2-carboxylic acid (2,6-difluoro-phenyl)-amide

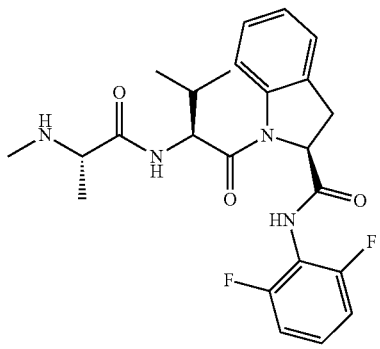 [SMILES: CN[C@@H](C)C(=O)N[C@H](C(=O)N1c2ccccc2C[C@H]1C(=O)Nc1c(F)cccc1F)C(C)C]

Step 1: N,N,N',N'-tetramethylfluoroformamidinium hexafluorophosphate (1.1 g, 4.18 mmol, Eq: 1.6) was added to a solution of (S)-2-(tert-butoxycarbonylamino)-3-methylbutanoic acid (738 mg, 3.4 mmol, Eq: 1.3) and diisopropylethylamine (1.4 mL, 7.84 mmol, Eq: 3) in DCM (10 mL) and the resulting solution was stirred at rt for 1 h. (S)-Ethyl indoline-2-carboxylate (0.5 g, 2.61 mmol, Eq: 1.00) was added and the reaction mixture was stirred at rt over the weekend. The reaction mixture was diluted with EtOAc (50 mL) and washed with 0.1 M aqueous HCl (50 mL), 0.1 M aqueous NaOH (50 mL) and brine (25 mL). The crude material was purified by flash chromatography (silica gel, 24 g, 0% to 20% EtOAc in hexanes) to give (S)-ethyl 1-((S)-2-(tert-butoxycarbonylamino)-3-methylbutanoyl)indoline-2-carboxylate (0.58 g), m/z=391 (M+H).

Step 2: Lithium hydroxide monohydrate (187 mg, 4.46 mmol, Eq: 3) in water (4.5 mL) was added to an ice-bath cooled solution of (S)-ethyl 1-((S)-2-(tert-butoxycarbonylamino)-3-methylbutanoyl)indoline-2-carboxylate (0.58 g, 1.49 mmol, Eq: 1.00) in THF (13.5 mL) and MeOH (4.5 mL). The cooling bath was removed and the reaction was stirred at rt for 1 h. 0.1 M Aqueous $KHSO_4$ (50 mL) was added to the reaction mixture and the resulting mixture was extracted with DCM (2×50 mL). The aqueous layer was further acidified with 1 M aqueous HCl (~5 mL) and extracted again with DCM (2×50 mL). The organic layers were combined, dried over $Na_2SO_4$ and concentrated in vacuo. The residue was azeotroped with hexanes to give (S)-1-((S)-2-(tert-butoxycarbonylamino)-3-methylbutanoyl)indoline-2-carboxylic acid (0.56 g), m/z=363 (M+H).

Step 3: Phosphorus oxychloride (164 mg, 0.1 mL, 1.07 mmol, Eq: 2.16) was added dropwise to a cooled (ice-bath) solution of 2,6-difluoroaniline (264 mg, 0.22 mL, 2.04 mmol, Eq: 4.12) and (S)-1-((S)-2-(tert-butoxycarbonylamino)-3-methylbutanoyl)indoline-2-carboxylic acid (0.18 g, 497 μmol, Eq: 1.00) in pyridine (4 mL). The cooling bath was removed and the reaction was stirred at rt. After 1 h the reaction mixture was diluted with toluene (10 mL) and concentrated in vacuo. The residue was treated with water (10 mL) and extracted with EtOAc (2×10 mL). The combined organic layers were washed with 0.1 M aqueous HCl (10 mL) and brine (10 mL) and then concentrated in vacuo. The crude material was purified by flash chromatography (silica gel, 12 g, 0% to 30% EtOAc in hexanes) to give tert-butyl (S)-1-((S)-2-(2,6-difluorophenylcarbamoyl)indolin-1-yl)-3-methyl-1-oxobutan-2-ylcarbamate (0.21 g), m/z=474 (M+H).

Step 4: TFA (2 mL, 26.0 mmol, Eq: 76.8) was added to a solution of tert-butyl (S)-1-((S)-2-(2,6-difluorophenylcarbamoyl)indolin-1-yl)-3-methyl-1-oxobutan-2-ylcarbamate (0.16 g, 338 μmol, Eq: 1.00) in DCM (2 mL) and the resulting solution was stirred at rt for 1 h. The reaction mixture was concentrated in vacuo and the residue was azeotroped with n-heptane (20 mL) to give a viscous oil (0.16 g) which was used directly without further purification. HATU (0.21 g, 552 μmol, Eq: 1.68) was added to a solution of (S)-1-((S)-2-amino-3-methylbutanoyl)-N-(2,6-difluorophenyl)indoline- 2-carboxamide 2,2,2-trifluoroacetate (0.16 g, 328 µmol, Eq: 1.00), (S)-2-(tert-butoxycarbonyl(methyl)amino)propanoic acid (0.1 g, 492 µmol, Eq: 1.5) and diisopropylethylamine (0.29 mL, 1.66 mmol, Eq: 5.06) in DMF (2 mL) and the reaction was stirred at rt for 30 min. The reaction mixture was diluted with EtOAc (20 mL) and washed with 0.1 M aqueous NaOH (10 mL) and 0.1 M aqueous HCl (10 mL). Hexanes (20 mL) were added to the organic layer and it was washed with water (3×10 mL) and brine. The organic layer was concentrated in vacuo and the resulting crude material was purified by flash chromatography (silica gel, 12 g, 0% to 50% EtOAc in hexanes) to give tert-butyl (S)-1-((S)-1-((S)-2-(2,6-difluorophenylcarbamoyl)indolin-1-yl)-3-methyl-1-oxobutan-2-ylamino)-1-oxopropan-2-yl(methyl)carbamate (0.15 g), m/z=559 (M+H).

Step 5: TFA (2 mL, 26.0 mmol, Eq: 96.7) was added to a solution of tert-butyl (S)-1-((S)-1-((S)-2-(2,6-difluorophenylcarbamoyl)indolin-1-yl)-3-methyl-1-oxobutan-2-ylamino)-1-oxopropan-2-yl(methyl)carbamate (0.15 g, 269 µmol, Eq: 1.00) in DCM (2 mL) and the resulting solution was stirred at rt for 1 hr. The reaction mixture was concentrated in vacuo and treated with minimal ether/hexanes to give (S)-1-[(S)-3-methyl-2-((S)-2-methylamino-propionylamino)-butyryl]-2,3-dihydro-1H-indole-2-carboxylic acid (2,6-difluoro-phenyl)-amide as a white solid (0.11 g), m/z=459 (M+H).

Example 13

Biochemical Assays

TR-FRET Assay for BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(ε-biotin)-OH 1:2 TFA ("Peptide A") was identified as a substrate for the TR-FRET assay by screening the 6× Histidine-tagged BIR2 domain and BIR3 domain of XIAP against a set of 29 peptides synthesized based on sequences reported by Sweeny et al. (*Biochemistry*, 2006, 45, 14740 14748). The peptides were labeled with the fluorescent tags FITC or TAMRA and Kd values were determined by fluorescence polarization assay. The sequence AVPIAQKSEK was identified as optimal for using in an assay. The peptide sequence was derivatized with biotin to provide AVPIAQKSEK-(ε-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is MRHHHHHHRDHFALDRPSETHADYLLRTGQVVDIS-DTIYPRNPAMYSEEARLKSF QNWPDYAHLTPRELA-SAGLYYTGIGDQVQCFACGGKLKNWEPGDRAWSEH-RRHF PNCFFVLGRNLNIRSE.

The sequence of the BIR3 domain used for the TR-FRET assay is MRHHHHHHRSDAVSSDRNFPNSTNL-PRNPSMADYEARIFTFGTWIYSVNK EQLARAGFYALGEGDKVKCFHCGGGLTD-WKPSEDPWEQHAKWYPGCKYL L EQKGQEYINNIHLTHSLEECLVRTT.

Ten nanomolar of 6× Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(ε-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 min. incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an $IC_{50}$ value for each test compound.

These values are listed below in Table 3.

TABLE 3

| | Systematic Name | Ic50 BIR2 | Ic50 BIR3 |
|---|---|---|---|
| 1 | (S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide | 0.0212 | >54.8 |
| 2 | (S)-1-[(S)-3-Methyl-2-((S)-2-methylamino-propionylamino)-butyryl]-2,3-dihydro-1H-indole-2-carboxylic acid amide hydrochloride | 2.179 | >54.8 |
| 3 | (S)-1-[(S)-3-Methyl-2-((S)-2-methylamino-propionylamino)-butyryl]-2,3-dihydro-1H-indole-2-carboxylic acid benzylamide | 11.18667 | >54.8 |
| 4 | (S)-1-[(S)-3-Methyl-2-((S)-2-methylamino-propionylamino)-butyryl]-2,3-dihydro-1H-indole-2-carboxylic acid 5-fluoro-2-methyl-benzylamide | 0.8835 | >54.8 |
| 5 | (S)-1-[(S)-3-Methyl-2-((S)-2-methylamino-propionylamino)-butyryl]-2,3-dihydro-1H-indole-2-carboxylic acid (2-benzoyl-phenyl)-amide | 1.4835 | >54.8 |
| 6 | (S)-1-[(S)-2-((S)-2-Methylamino-propionylamino)-2-phenyl-acetyl]-2,3-dihydro-1H-indole-2-carboxylic acid 5-fluoro-2-methyl-benzylamide hydrochloride | 0.19 | >54.8 |
| 7 | (S)-1-[(S)-2-((S)-2-Methylamino-propionylamino)-2-phenyl-acetyl]-2,3-dihydro-1H-indole-2-carboxylic acid amide hydrochloride | 0.368 | >54.8 |
| 8 | (S)-1-[(S)-2-((S)-2-Methylamino-propionylamino)-2-phenyl-acetyl]-2,3-dihydro-1H-indole-2-carboxylic acid phenylamide hydrochloride | 0.226 | >54.8 |
| 9 | (S)-1-[(S)-2-((S)-2-Methylamino-propionylamino)-2-phenyl-acetyl]-2,3-dihydro-1H-indole-2-carboxylic acid biphenyl-2-ylamide hydrochloride | 0.135 | >54.8 |
| 10 | (S)-1-[(S)-2-((S)-2-Methylamino-propionylamino)-2-phenyl-acetyl]-2,3-dihydro-1H-indole-2-carboxylic acid (2-methoxy-phenyl)-amide hydrochloride | 0.174 | >54.8 |
| 11 | (S)-1-[(S)-2-((S)-2-Methylamino-propionylamino)-2-phenyl-acetyl]-2,3-dihydro-1H-indole-2-carboxylic acid benzylamide | 0.723 | 33.17 |
| 12 | (S)-1-[(S)-3-Methyl-2-((S)-2-methylamino-propionylamino)-butyryl]-2,3-dihydro-1H-indole-2-carboxylic acid (2,6-difluoro-phenyl)-amide | 0.053 | >54.8 |

The invention claimed is:
1. A compound of Formula I:

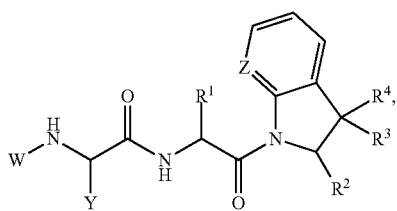

wherein
W is selected from the group
  a) $C_{1-6}$-alkyl that optionally includes 1-3 deuterium atoms,
  b) $C_{1-6}$-alkyl that optionally may be substituted with $SO_2R^5$ and $OR^5$
Y is $C_{1-6}$-alkyl;
Z is CH;
$R^1$ is selected from the group
  a) $C_{1-6}$-alkyl, and
  b) aryl;
$R^2$ is $CONHR^6$;
$R^3$ and $R^4$ may be the same or different and each is independently selected from the group
  a) H, and
  b) $C_{1-6}$-alkyl;
$R^5$ is selected from the group
  a) $C_{1-6}$-alkyl, and
  b) aryl;
$R^6$ is selected from the group
  a) H
  b) aryl that optionally may be substituted with $C_{1-6}$-alkyl, $OR^5$, halogen, aryl, and $C(O)R^7$, and
  c) $C_{1-6}$-alkyl that optionally may be substituted with aryl that optionally may be substituted with $C_{1-6}$-alkyl and halogen;
$R^7$ is selected from the group
  a) $C_{1-6}$-alkyl, and
  b) aryl;
or a pharmaceutically acceptable salt thereof.
2. The compound of claim 1 wherein W and Y are both $C_{1-6}$-alkyl, or a pharmaceutically acceptable salt thereof, or a pharmaceutically acceptable salt thereof.
3. The compound of claim 2 wherein both W and Y are methyl, or a pharmaceutically acceptable salt thereof.
4. The compound according claim 1, wherein $R^1$ is $C_{1-6}$-alkyl, or a pharmaceutically acceptable salt thereof.
5. The compound of claim 4 wherein $R^1$ is propanyl, or a pharmaceutically acceptable salt thereof.
6. The compound according to claim 1, where $R^1$ is aryl, or a pharmaceutically acceptable salt thereof.
7. The compound of claim 6 wherein $R^1$ is phenyl, or a pharmaceutically acceptable salt thereof.
8. The compound according to claim 1, wherein $R^3$ and $R^4$ are H, or a pharmaceutically acceptable salt thereof.
9. The compound according to claim 1, wherein one or both $R^3$ and $R^4$ are $C_{1-6}$-alkyl.
10. The compound according to claim 1, where $R^5$ is $C_{1-6}$-alkyl, or a pharmaceutically acceptable salt thereof.
11. The compound of claim 10 wherein $R^5$ is methyl, or a pharmaceutically acceptable salt thereof.
12. The compound according to claim 1, wherein $R^5$ is aryl, or a pharmaceutically acceptable salt thereof, or a pharmaceutically acceptable salt thereof.
13. The compound of claim 12 wherein $R^5$ is phenyl, or a pharmaceutically acceptable salt thereof.
14. The compound according to claim 1, wherein $R^6$ is aryl that optionally may be substituted with $OR^5$, halogen, and aryl, or a pharmaceutically acceptable salt thereof.
15. The compound according to claim 1, wherein $R^6$ is $C_{1-6}$-alkyl that optionally may be substituted with phenyl that optionally may be substituted with $C_{1-6}$-alkyl and halogen, or a pharmaceutically acceptable salt thereof.
16. The compound of claim 1 wherein W, Y and $R^1$ are $C_{1-6}$-alkyl, $R^2$ is $CONHR^6$, and $R^6$ is aryl that optionally may be substituted with aryl, $C_{1-6}$-alkyl, and $OR^5$, or a pharmaceutically acceptable salt thereof.
17. The compound of claim 1 wherein W, Y and $R^1$ are $C_{1-6}$-alkyl, $R^2$ is $CONHR^6$, and $R^6$ is H, or a pharmaceutically acceptable salt thereof.
18. The compound of claim 1 wherein W, Y and $R^1$ are $C_{1-6}$-alkyl, $R^2$ is $CONHR^6$, and $R^6$ is $C_{1-6}$-alkyl that optionally may be substituted with phenyl that optionally may be substituted with halogen, or a pharmaceutically acceptable salt thereof.
19. The compound of claim 1 wherein W, Y are $C_{1-6}$-alkyl, $R^1$ is aryl, $R^2$ is $CONHR^6$, and $R^6$ is aryl that optionally may be substituted with aryl, $C_{1-6}$-alkyl, halogen and $OR^5$, or a pharmaceutically acceptable salt thereof.
20. The compound of claim 19 wherein $R^6$ is phenyl that optionally may be substituted with phenyl and $OR^5$, or a pharmaceutically acceptable salt thereof.
21. The compound of claim 1 wherein W, Y are $C_{1-6}$-alkyl, $R^1$ is aryl, $R^2$ is $CONHR^6$, and $R^6$ is $C_{1-6}$-alkyl that optionally may be substituted with aryl that optionally may be substituted with halogen, or a pharmaceutically acceptable salt thereof.
22. The compound of claim 1 wherein W, Y are $C_{1-6}$-alkyl, $R^1$ is aryl, $R^2$ is $CONHR^6$, and $R^6$ is H, or a pharmaceutically acceptable salt thereof.
23. A compound selected from the group consisting of:
  (S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide;
  (S)-1-[(S)-3-Methyl-2-((S)-2-methylamino-propionylamino)-butyryl]-2,3-dihydro-1H-indole-2-carboxylic acid amide hydrochloride;
  (S)-1-[(S)-3-Methyl-2-((S)-2-methylamino-propionylamino)-butyryl]-2,3-dihydro-1H-indole-2-carboxylic acid benzylamide;

(S)-1-[(S)-3-Methyl-2-((S)-2-methylamino-propionylamino)-butyryl]-2,3-dihydro-1H-indole-2-carboxylic acid 5-fluoro-2-methyl-benzylamide;

(S)-1-[(S)-3-Methyl-2-((S)-2-methylamino-propionylamino)-butyryl]-2,3-dihydro-1H-indole-2-carboxylic acid (2-benzoyl-phenyl)-amide;

(S)-1-[(S)-2-((S)-2-Methylamino-propionylamino)-2-phenyl-acetyl]-2,3-dihydro-1H-indole-2-carboxylic acid 5-fluoro-2-methyl-benzylamide hydrochloride;

(S)-1-[(S)-2-((S)-2-Methylamino-propionylamino)-2-phenyl-acetyl]-2,3-dihydro-1H-indole-2-carboxylic acid amide hydrochloride;

(S)-1-[(S)-2-((S)-2-Methylamino-propionylamino)-2-phenyl-acetyl]-2,3-dihydro-1H-indole-2-carboxylic acid phenylamide hydrochloride;

(S)-1-[(S)-2-((S)-2-Methylamino-propionylamino)-2-phenyl-acetyl]-2,3-dihydro-1H-indole-2-carboxylic acid biphenyl-2-ylamide hydrochloride;

(S)-1-[(S)-2-((S)-2-Methylamino-propionylamino)-2-phenyl-acetyl]-2,3-dihydro-1H-indole-2-carboxylic acid (2-methoxy-phenyl)-amide hydrochloride;

(S)-1-[(S)-2-((S)-2-Methylamino-propionylamino)-2-phenyl-acetyl]-2,3-dihydro-1H-indole-2-carboxylic acid 5-fluoro-2-methyl-benzylamide hydrochloride; and (S)-1-[(S)-3-Methyl-2-((S)-2-methylamino-propionylamino)-butyryl]-2,3-dihydro-1H-indole-2-carboxylic acid (2,6-difluoro-phenyl)-amide; or a pharmaceutically acceptable salt of any of the foregoing compounds.

24. A compound selected from the group consisting of:

(S)-3,3-Dimethyl-1-[(S)-3-methyl-2-((S)-2-methylamino-propionylamino)-butyryl]-2,3-dihydro-1H-indole-2-carboxylic acid (2,6-difluoro-phenyl)-amide; and (S)-1-[(S)-3-Methyl-2-((S)-2-methylamino-propionylamino)-butyryl]-2,3-dihydro-1H-indole-2-carboxylic acid (2,6-difluoro-phenyl)-amide; or a pharmaceutically acceptable salt of either of the foregoing compounds.

25. A pharmaceutical composition comprising a compound according to claim 1, or a pharmaceutically acceptable salt thereof, as an active ingredient together with a pharmaceutically acceptable carrier or excipient.

* * * * *

SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: TR-FRET peptide

<400> SEQUENCE: 1

Ala Val Pro Ile Ala Gln Lys Ser Glu Lys
1               5                   10

<210> SEQ ID NO 2
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 2

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
            20                  25                  30

Asp Ile Ser Asp Thr Ile Tyr Pro Arg Asn Pro Ala Met Tyr Ser Glu
        35                  40                  45

Glu Ala Arg Leu Lys Ser Phe Gln Asn Trp Pro Asp Tyr Ala His Leu
    50                  55                  60

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
        115                 120                 125

<210> SEQ ID NO 3
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 3

Met Arg His His His His His His Arg Ser Asp Ala Val Ser Ser Asp
1               5                   10                  15

Arg Asn Phe Pro Asn Ser Thr Asn Leu Pro Arg Asn Pro Ser Met Ala
            20                  25                  30

Asp Tyr Glu Ala Arg Ile Phe Thr Phe Gly Thr Trp Ile Tyr Ser Val
        35                  40                  45

Asn Lys Glu Gln Leu Ala Arg Ala Gly Phe Tyr Ala Leu Gly Glu Gly
    50                  55                  60

Asp Lys Val Lys Cys Phe His Cys Gly Gly Gly Leu Thr Asp Trp Lys
65                  70                  75                  80

Pro Ser Glu Asp Pro Trp Glu Gln His Ala Lys Trp Tyr Pro Gly Cys
                85                  90                  95

```
Lys Tyr Leu Leu Glu Gln Lys Gly Gln Glu Tyr Ile Asn Asn Ile His
            100                 105                 110
Leu Thr His Ser Leu Glu Glu Cys Leu Val Arg Thr Thr
            115                 120                 125
```